United States Patent [19]

Bolduc et al.

[11] E Re. 29,207

[45] Reissued May 10, 1977

[54] DISPENSING METHOD AND APPARATUS

[75] Inventors: Lee R. Bolduc, St. Louis Park; Eugene A. Dickhudt, St. Paul, both of Minn.

[73] Assignee: Population Research Incorporated, Minneapolis, Minn.

[22] Filed: Jan. 24, 1975

[21] Appl. No.: 543,875

Related U.S. Patent Documents

Reissue of:

[64] Patent No.: 3,822,702
Issued: July 9, 1974
Appl. No.: 372,971
Filed: June 25, 1973

[52] U.S. Cl. ..... 128/235; 128/260; 128/130; 128/1 R; 128/349 B

[51] Int. Cl.[2] ..... A61M 1/00

[58] Field of Search ..... 128/235, 234, 232, 224, 128/240, 241, 246, 260, 216, 218, 349, 127, 129, 130, 1, 303, 341

[56] References Cited

UNITED STATES PATENTS

| | | | |
|---|---|---|---|
| 2,696,212 | 12/1954 | Dunmire | 128/216 |
| 2,699,167 | 1/1955 | Raiche | 128/216 |
| 2,854,982 | 10/1958 | Pagano | 128/349 BV |
| 3,042,030 | 7/1962 | Read | 128/127 |
| 3,211,151 | 10/1965 | Foderick et al. | 128/349 B |
| 3,394,705 | 7/1968 | Abramson | 128/349 B |
| 3,401,689 | 9/1968 | Greenwood | 128/129 |
| 3,422,813 | 1/1969 | Braley et al. | 128/1 R |
| 3,452,749 | 7/1969 | Riedell | 128/129 |
| 3,459,175 | 8/1969 | Miller | 128/349 B |
| 3,680,542 | 8/1972 | Cimber | 128/1 R |
| 3,817,248 | 6/1974 | Buckles et al. | 128/260 |

OTHER PUBLICATIONS

"The Effect of Methyl Cyanoacrylate Tissue Adhesive on the Human Fallopian Tube and Endometrium" by T. C. Stevenson et al., Journal of Obstetrics and Gynaecology of the British Commonwealth, Nov. 1972, vol. 79, pp. 1028–1039.

*Primary Examiner*—John D. Yasko
*Attorney, Agent, or Firm*—Lindquist & Vennum

[57] ABSTRACT

A fluid dispensing instrument and method for introducing a fluid, as drug materials, into the canals of the Fallopian tubes of a primate female. The dispensing instrument has a tubular probe carrying an expandable balloon assembly. A stop collar on the probe positions the balloon assembly in the uterine cavity. The balloon assembly has a sleeve member which is initially expanded to close the lower portion of the uterine cavity. The drug material is introduced through the probe into the upper portion of the uterine cavity above the expanded balloon assembly. The balloon assembly is then further expanded to force the drug material from the upper portion of the uterine cavity into the canals of the Fallopian tubes. The expanding balloon assembly divides the material and forces the drug material into both of the canals.

42 Claims, 3 Drawing Figures

DISPENSING METHOD AND APPARATUS

Matter enclosed in heavy brackets [ ] appears in the original patent but forms no part of this reissue specification; matter printed in italics indicates the additions made by reissue.

BACKGROUND OF INVENTION

Bilateral disection of Fallopian tubes is a common surgical procedure used to sterilize a female primate. This procedure involves severing and tying the Fallopian tubes. Intrauterine devices, as plugs and wires, are used to temporarily sterilize a female. These devices include plugs which are inserted into the canals of the Fallopian tubes to prevent ova from passing the canals into the uterus. Smith in 1849 described a method to treat sterility by passing whale bone splints into the canals. These devices do not insure that the ova cannot flow through the canels into the uterus. The devices can be dislodged and lost without the female being aware of it. There is no assurance that the devices are effective. Climer in U.S. Pat. No. 3,675,693 and No. 3,680,245 discloses plugs attached to the uterine wall to block the entrance of ova into the uterus from the Fallopian canals and the exit of sperm from the uterine cavity into the Fallopian canal. These plugs are designed to effect temporary sterilization in that they can be removed and do not permanently block the canals of the Fallopian tubes. Plug contraceptive devices are not entirely effective in that it is possible for ova to bypass the plugs and enter the uterus.

Liquid tissue adhesives have been developed which polymerize when applied to moist living tissue. These adhesives have been used for various surgical procedures. When the tissue adhesives are used, the cells adjacent the tissue are damaged and eventually replaced with a fibrous tissue. A liquid tissue adhesive has been injected into the uterine cavity with a catheter to occlude the canals of the Fallopian tubes. Studies have been conducted into silver nitrate, zinc chloride and methyl cyanoacrylate to occlude the canals of the Fallopian tubes. These materials have been introduced into the uterine cavity with balloon catheters in an effort to place the materials in the canals of the Fallopian tubes. These catheters are not designed to accommodate the different sizes, shapes and characteristics of the uteri and do not insure that the materials are placed in each canal of the Fallopian tubes. Also, these catheters may direct all the material into one canal so that the material is forced through this canal into the body cavity. *Examples of prior art balloon catheters may be found in "The Effect of Methyl Cyanoacrylate Tissue Adhesive on the Human Fallopian Tube and Endometrium," by Stevenson, et al, "The Journal of Obstetrics and Gynecology of the British Commonwealth," November, 1972, Vol. 79, pp. 1028–1039, "Human Sterilization," edited by Richart and Prager, 1972, and "Female Sterilization," edited by Duncan, et al, 1972, (see p. 107 e.g.).*

SUMMARY OF INVENTION

The invention is directed to an apparatus and method for dispensing a fluid, as a drug material, into both canals of the Fallopian tubes of a primate female. More specifically, the invention is directed to a method of introducing a predetermined minimum amount of tissue adhesive into both canals of the Fallopian tubes of a primate female. The apparatus has an elongated probe having a forward end attached to an expandable balloon assembly. A stop collar on the probe functions to position the balloon assembly in the uterine cavity with the forward end of the balloon assembly spaced from the top wall or fundus of the uterus. A dispenser operates to initially expand the balloon assembly to displace the lower portion of the uterine cavity and form a low pressure seal with the inner wall of the lower part of the uterus. The balloon assembly can be fully expanded to sense the size of the uterine cavity. The balloon assembly is partially contracted to maintain a low pressure seal with the inner wall of the lower part of the uterus.

The dispenser is then again actuated to discharge a drug material, as a tissue adhesive, into the uterine cavity above the balloon assembly. The balloon assembly is then further expanded to displace the remaining space of the uterine cavity. The balloon assembly expands and initially engages the midportion of the fundus and thereby divides the drug material into separate portions. The further expansion of the balloon assembly forces the separate portions of the drug material into the separate canals of the Fallopian tubes. Substantially all of the drug materials introduced into the uterine cavity is moved into the canals of the Fallopian tubes on expansion of the balloon assembly. When a tissue adhesive is placed into the canals it reacts with the moisture in the tissue of the Fallopian tubes to polymerize the adhesive and thereby occlude the canals. The tissue adhesive is eventually replaced with scar tissue which permanently occludes the canals. A flushing fluid, as water, can be introduced into the uterine cavity before the balloon assembly is removed from the cavity. The balloon assembly is contracted whereby it can be readily removed from the uterine cavity.

An object of the invention is to provide an apparatus and method of introducing a predetermined minimum amount of drug materials into both canals of the Fallopian tubes of a primate female from the uterine cavity. Another object of the invention is to provide a method and apparatus for introducing a controlled amount of drug material into the canals of the Fallopian tubes under low pressure, whereby the drug material does not flow through the Fallopian tubes into the body cavity. A further object of the invention is to provide a method and apparatus for introducing drug materials into the canals of the Fallopian tubes which places a minimum amount of force on the walls of the uterus and which can accommodate different sizes, shapes and characteristics of uteri. Yet another object of the invention is to provide a method and apparatus for introducing a fluid material into both canals of the Fallopian tubes which is not position sensitive and does not apply substantial pressures to the fluid material whereby the fluid material is not forced into the blood stream.

IN THE DRAWINGS

Figure 1:
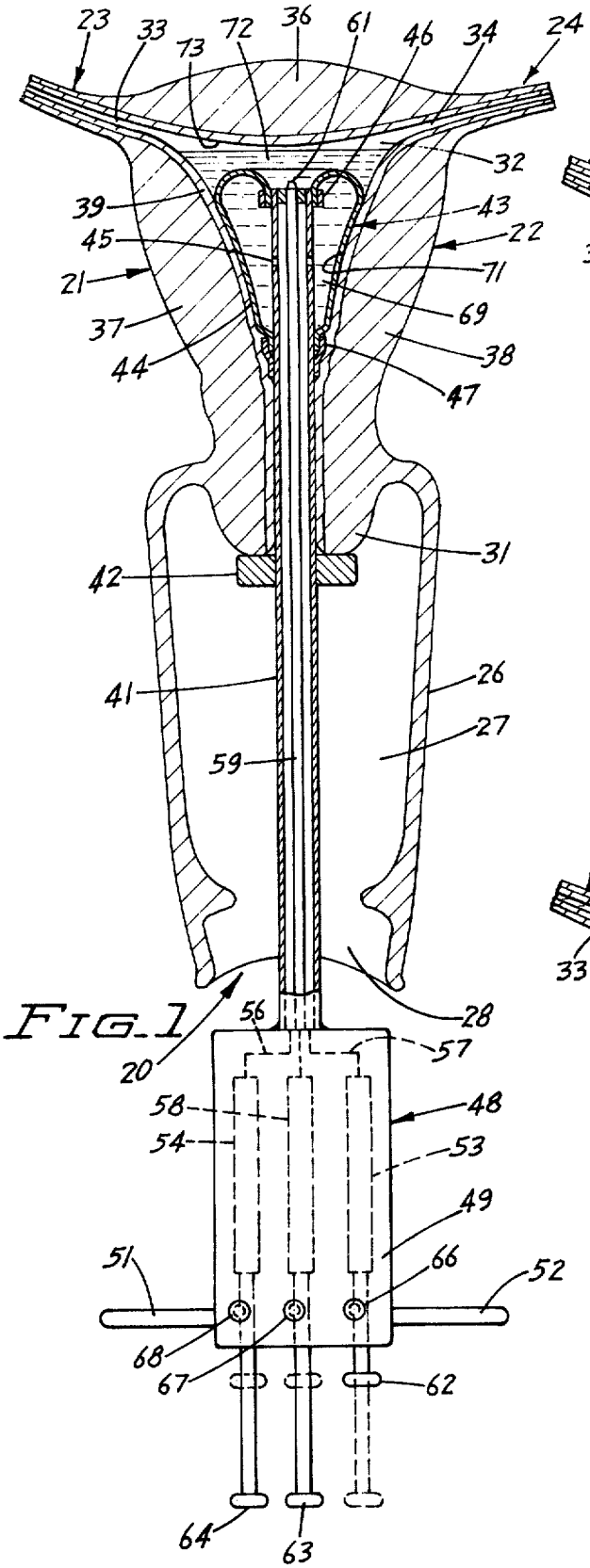
FIG. 1 is a sectional view of the reproductive system of a primate female accommodating a dispensing instrument to practice the method of the invention of locating drug material in both canals of the Fallopian tubes.

Referring to the drawings, as shown in FIG. 1, a dispensing instrument indicated generally at 20 in operative relation with the female reproductive system indicated generally at 21 of a primate female. System 21 has a uterus 22 and a pair of Fallopian tubes 23 and 24. The lower part of uterus 22 is integral with an elongate vagina 26. The vagina 26 has a vaginal cavity 27 having an opening or entrance 28. The opposite end of the cavity 27 is in communication with the cervix 31 having a cervical opening providing a passage from the vaginal cavity 27 into the uterine cavity 32. The Fallopian tubes 23 and 24 each have a canal or aqueduct 33 and 34 respectively, which open or exit to the upper part of the uterine cavity 32.

Uterus 22 is a generally pear-shaped, thick-walled, hollow organ situated between the bladder and rectum. The uteri of primate females vary in size and shape. The wall thicknesses, strength and sensitivity to pain vary from female to female. The inner wall of the uterus may contain lymph nodes and vary in size and configuration. The uterine cavities of the uteri vary in size and shape. Some uteri have strong walls while others have weak and relatively elastic walls. Generally, the uterine cavity 32 is flattened and triangular in shape.

The Fallopian tubes 23 and 24 are paired, trumpet-shaped, muscular linear members which extend from the superior angles of the uterine cavity to the ovaries (not shown). The Fallopian tubes of an adult female are musculo-membranous structures about 12 cm. in length. The outlet of the canals of the Fallopian tubes can vary in position relative to the uterine cavity 32. Also, the size of the canals 33 and 34 vary from female to female. The Fallopian tubes are commonly divided into isthmus, intramural and ampullary sections. The canals 33 and 34 provide passages for movement of ova from the ovaries into the uterine cavity 32. The intramural sections of the Fallopian tubes traverse the uterine wall in more or less straight fashion. It has an ampullalike dilation just before it communicates with the uterine cavity 32. The walls of the Fallopian tubes consist of three layers, the serosal layer, the muscular layer, and the mucosal lining. The muscular layer includes longitudinal muscle fibers which, when contracted, bring the outer ends of the Fallopian tubes into close contact with the surfaces of the ovaries. Blood vessels are abundant in the muscular layer where they form with the muscle bundles a kind of erectile tissue which, if engorged with blood, move the Fallopian tubes to sweep over the surfaces of the ovaries. This movement of the Fallopian tubes is impaired when the tubes are severed and tied. The occluding of the canals 33 and 34 with drug material according to the invention does not interfere with the erectile action and movement of the Fallopian tubes relative to the ovaries.

The uterus 21 has a top wall or fundus 36 and side walls 37 and 38 surrounding the uterine cavity 32. The inside of the top wall 36 and the side walls 37 and 38 have an inside lining or membrane 39 which periodically is sloughed off in the normal cycle of the female.

The dispensing instrument 20 has an elongated probe or tubular support 41 of a length to pass through the vaginal cavity 27 and into the uterine cavity 32. The longitudinal position of the probe 41 relative to the uterine cavity 32 is determined by an annular stop member or collar 42. The collar 42 is secured to the probe 41 adjacent the inner end of an expandable balloon assembly indicated generally at 43.

Balloon assembly 43 has a sleeve member or tubular membrane 44. The upper or outer end of the member 44 is secured to the support 41 with an annular fastener as a collar or threads 46. A similar annular fastener 47 secures the inner end of the sleeve member 44 to the probe 41. The probe 41 has a plurality of openings 45 to provide for communication of fluid from within the probe 41 to the chamber 69 surrounded by the sleeve member 44.

Figure 2:
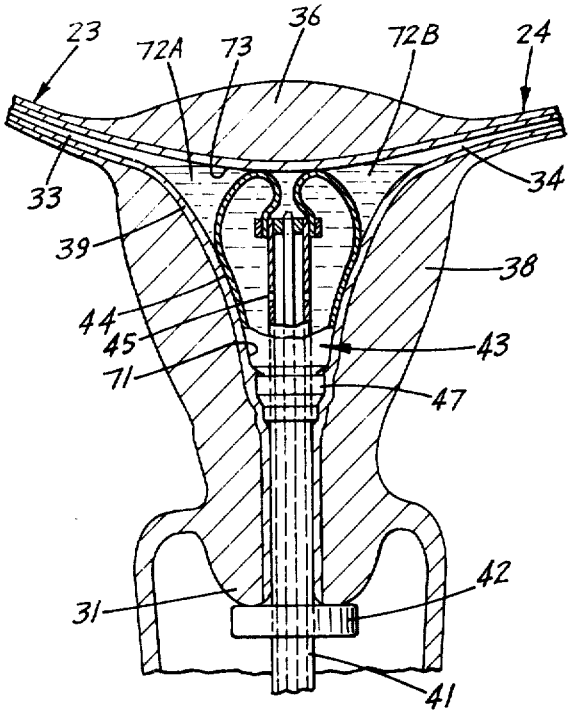
FIG. 2 is a sectional view of the uterus of FIG. 1 showing the balloon in an expanded position to divide the uterine cavity.
Figure 3:
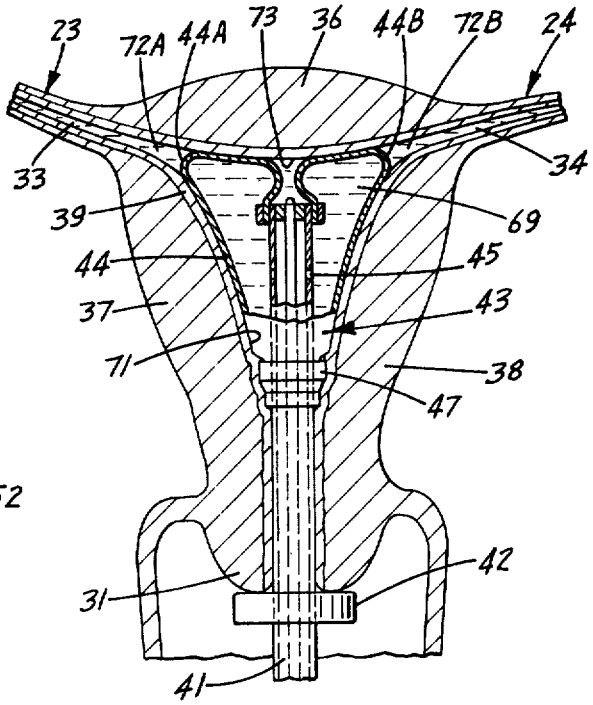
FIG. 3 is a sectional view similar to FIG. 2 showing the balloon in the full expanded position forcing the drug material into both canals of the Fallopian tubes.

The sleeve member 44 is a tubular sheet member of soft and relaxed flexible and elastic material, as rubber or plastic, which expands with a minimum of elongation of the material. For example, this latex rubber having low surface tension, whereby the rubber uniformly expands with a relatively low pressure, is suitable material for sleeve member 44. The material of sleeve member 44 readily expands to displace the uterine cavity 32 by conforming to the shape of the cavity without applying extreme pressure to localized portions of the uterus. When the cavity 32 is partially displaced and fully displaced with the expanded sleeve member 44, as shown in FIGS. 1, 2 and 3, the member 44 is in uniform surface engagement with the inside wall 39. Conventional balloon catheters, being of hard, relatively non-elastic material, do not assume the configuration of the uterine cavity when expanded under low pressure.

A dispenser indicated generally at 48 is secured to the outside end of probe 41. Dispenser 48 has a housing or body 49. A pair of oppositely directed handles 51 and 52 are secured to the body to serve as finger grips in the use of the instrument. The housing 49 has chambers for accommodating containers 53 and 54 connected with passages 56 and 57, respectively. The passages 56 and 57 are open to the passage in the probe 41. Located between containers 53 and 54 is a third container 58. Container 58 is adapted to be coupled to elongated tube 59 extended longitudinally through the probe 41. Tube 59 has an outer or discharge end 61 at the outer end of the balloon assembly 43. Plungers 62, 63, and 64, slideably mounted on the housing 49, are operable to apply forces to the containers 53, 54 and 58 and thereby discharge the fluids in the containers via the probe 41 to the balloon assembly 43 or the uterine cavity 32. Each plunger has a separate lock 66, 67 and 68 respectively which holds the plunger in its inactive position. The locks are manually released, which enables the plungers 62, 63 and 64 to be moved into the housing 49 and thereby apply forces to the containers associated with the plungers.

Dispenser 48 can be constructed in accordance with the dispenser as shown in FIGS. 1 to 10 in pending U.S. Pat. application Ser. No. 361,418. The disclosure of this application is incorporated herein by reference. Other types of dispensers can be used to provide fluid under pressure to the balloon assembly 43 and discharge drug materials, tissue adhesives and the like into the uterine cavity 32.

For example the dispensing apparatus disclosed in pending U.S. applications Ser. No. 339,911 and Ser. No. 361,418 can be used to expand the balloon assembly 43 and discharge drug material into the uterine cavity. The disclosures of these applications are incorporated herein by reference.

The tissue adhesive can be cyanoacrylate, silver nitrate, quinacrine material and like material used as surgical glues. The cyanoacrylate is a liquid plastic which sets up or polymerizes in response to moisture and thereby functions to occlude the canals of the Fallopian tubes. The cyanoacrylates include, but are not limited to, methyl cyanoacrylate, methyl-2-cyanoacrylate, ethyl cyanoacrylates, n-propyl cyanoacrylates, n-butyl cyanoacrylates, n-amyl cyanoacrylates, n-hexl cyanoacrylates, n-heptyl cyanoacrylates, isobutyl-2-cyanoacrylates and n-octyl cyanoacrylates, quinacrine material is a relatively thick or heavy fluid in the nature of a semi-fluid. The pumping action due to the expansion of the sleeve member 44, hereinafter described, in the uterine cavity 32 is effective in moving this material from the uterine cavity into the canals of the Fallopian tubes. The drugs can be of the type that temporarily block or occlude the canals of the Fallopian tubes. After a period of time, the canals will reopen to resume their normal function.

In use, the dispensing instrument 20 is loaded with the containers 53, 54 and 58. The containers can be preloaded prior to the operating procedure. With the patient in the reclined position, the collapsed balloon assembly 43 is moved through the vaginal cavity 27 and through the cervical opening in to the uterine cavity 32. This located the balloon assembly 43 in the lower part of the uterine cavity 32. The probe 41 is moved up into the uterus until the collar 42 is located against the cervix 31, as shown in FIG. 1. The balloon assembly, being in a deflated condition, slides readily through the cervical opening and into the uterine cavity 32. The balloon assembly 43 shown in FIG. 1 is positioned in the central longitudinal position. This position is not always achieved in the insertion procedure. The balloon asssembly 43 may be located on either side and extend at an angle toward one of the Fallopian tubes. The method hereinafter described is operable to move drug materials into both canals regardless of the position of the balloon assembly 43 in the uterine cavity. In other words, to be operable, the balloon assembly is not position sensitive.

The sleeve member 44 then is expanded by introducing fluid, either liquid or air, under pressure into the balloon cavity 69. The sleeve member 44 is partially expanded to fill the lower part of the uterine cavity 32 to form a seal with the inner surface 71 of the side walls 37 and 38. The top of the balloon assembly 43 is spaced from the inner wall of the fundus 36. The sleeve member 44 is initially expanded by releasing the lock 66. This permits the plunger 62 to move into the housing 49, forcing the fluid in the container 53 into the balloon chamber 69 via the probe 41. Sleeve member 44 of the balloon assembly being of a low tension expandable material, places uniform low pressure on the inner surface 71 of the uterus and assumes the shape of the lower part of the uterine cavity without subjecting any specific portion of the uterus to substantial pressure.

Balloon assembly 43 can be fully expanded to sense the size of the uterine cavity 32. The balloon assembly 43 is partially reduced in size to move it away from the inner wall 73 of the fundus, thereby leaving a space between the inner wall 73 and the partially expanded balloon assembly 43, as shown in FIG. 1.

Drug material 72 is then dispensed from container 58 by releasing the lock 67. The plunger 63 applies force on the container 58 to move a controlled amount of material from the container 58 into the tube 59. The drug material is discharged into the upper end of the uterine cavity 32, as illustrated by the broken lines and reference numeral 72. Material 72 is located in the space between the inner wall 73 and the expanded balloon assembly 43 and is subjected to only a small amount of pressure.

Referring to FIG. 2, the sleeve member 44 is further expanded until it engages the inner wall 73 of the fundus 36. The expanding sleeve member 44 divides the drug material 72 into two substantially equal portions 72a and 72b. The sleeve member 44 expands into a cylindrical or egg-shaped configuration and initially engages the midportion of the inner wall 73.

Referring to FIG. 3, the sleeve member 44 is further expanded by introducing additional fluid into the balloon chamber 69. The sleeve member 44 expands to fill or displace the portions of the uterine cavity leading to the canals 33 and 34 of the Fallopian tubes. The expansion of the sleeve member 44 forces the drug materials 72a and 72b under low pressure into the canals 33 and 34. In other words, the expanding sleeve member 44 functions as a diaphragm pump to force or move the drug materials 72a and 72b into the canals 33 and 34 respectively. The sleeve member 44, being in firm engagement with the inside surface 71 and the inner wall 73, prevents the drug materials 72a and 72b from remaining in the uterine cavity 32. As it expands, the sleeve member 44 does not block or hold drug material as it pushes the drug material into the canals of the Fallopian tubes.

When drug materials of the tissue adhesive type are used, the canals 33 and 34 will be permanently occluded. The tissue adhesives, as the cyanoacrylate type, cause fibroplastic proliferation which in time will histologically close the canals 33 and 34. The tissue adhesives polymerize when subjected to moist living tissue. The cells adjacent the tissue are damaged and eventually replaced by fibrous tissue.

The sleeve member 44 then is contracted to about the position shown in FIG. 1. A second fluid, as water, is then injected into the uterine cavity 32 to dilute and wash away any drug material that remains in the cavity 32. The sleeve member 44 is then completely contracted by allowing the fluid in the balloon chamber 69 to drain back into the dispenser 48 or into a reservoir or container attached to the dispenser. When the fluid from chamber 69 has been evacuated, the balloon assembly is withdrawn from the uterine cavity 32 to conclude the operation.

While there have been shown and described a preferred embodiment of the dispensing instrument and method of introducing drug material into both canals of the Fallopian tubes of a primate female, it is understood that various changes in the structure and method may be made by those skilled in the art without departing from the spirit of the invention.

The embodiments of the invention in which an exclusive property or privilege is claimed are defined as follows:

1. A method of placing material in both canals of Fallopian tubes open to the uterine cavity of a uterus with an expandable balloon assembly comprising: introducing the balloon assembly into the uterine cavity, expanding the balloon assembly into engagement with the inside side walls of the uterus and spaced from the inside top wall of the uterus, discharging material into the uterine cavity between the expanded balloon assembly and the inside top wall of the uterus, further expanding the balloon assembly into engagement with the top inside wall of the uterus dividing the material into two portions and forcing one portion into one canal with one part of the balloon assembly and the other portion into the other canal with the other portion of the balloon assembly, contracting the balloon assembly, and removing the contracted balloon assembly from the uterine cavity.

2. The method of claim 1 wherein: the balloon assembly is introduced into the uterine cavity to a selected position with the balloon assembly spaced from the inside top wall of the uterus.

3. The method of claim 2 wherein: the balloon assembly is held in the selected position during the discharge of material in the uterine cavity.

4. The method of claim 1 wherein: the balloon assembly during the further expansion thereof initially engages the central section of the inside top wall of the uterus dividing the uterine cavity into two parts.

5. The method of claim 1 including: discharging a second material into the uterine cavity before the balloon assembly is contracted.

6. A method of placing material in both canals of Fallopian tubes open to the uterine cavity with an expandable sleeve member comprising: introducing the sleeve member into the uterine cavity, expanding the sleeve member into engagement with the inside side walls and top wall of the uterus to displace the uterine cavity, contracting the expanded sleeve member to move the sleeve member out of engagement with the inside top wall of the uterus, discharging material into the uterine cavity between the contracted sleeve member and the inside top wall of the uterus, expanding the sleeve member to displace the uterine cavity by moving the sleeve member into engagement with the inside top wall of the uterus thereby dividing the material into two portions and forcing one portion into one canal with one part of the sleeve member and the other portion into the other canal with another part of the sleeve member, contracting the sleeve member, and removing the contracted sleeve member from the uterine cavity.

7. The method of claim 6 wherein: the sleeve member is introduced into the uterine cavity to a selected position spaced from the inside top wall of the uterus.

8. The method of claim 6 wherein: the sleeve member during the second expansion thereof to fully displace the uterine cavity initially engages the central section of the inside top wall of the uterus dividing the uterine cavity into two parts.

9. The method of claim 6 including: discharging a second material into the uterine cavity after the first material has been moved into the canals and before the sleeve member is contracted for removal from the uterine cavity.

10. An appartus for placing material in both canals of Fallopian tubes comprising: a balloon assembly having an expandable sleeve member, elongated means supporting the balloon assembly, means on the elongated means to position the balloon assembly in the uterine cavity spaced from the inside top wall of the uterus, first means operable to expand the sleeve member into engagement with the inside side walls of the uterus, second means for discharging material into the uterine cavity between the expanded sleeve member and the inside top wall of the uterus, said first means being operable to further expand the sleeve member into engagement with the inside top wall of the uterus whereby the material is divided into two separate portions, said further expansion of the sleeve member forcing one portion into one canal of one Fallopian tube and the other portion into the other canal of the other Fallopian tube.

11. The apparatus of claim 10 wherein: the sleeve member is made of expandable tubular sheet material having low surface tension properties.

12. The apparatus of claim 11 wherein: the means on the elongated means is an annular collar.

13. The apparatus of claim 10 wherein: the elongated means is a tubular member connected to the first means and second means.

*14. Apparatus for non-surgically providing materials into the Fallopian tubes of a female body comprising: first means for dispensing material into a uterine cavity; and second means selectively operable within the uterine cavity for moving the dispensed material from the uterine cavity into both Fallopian tubes.*

*15. The apparatus of claim 14 in which: the second means comprises pump means selectively operable to force the dispensed material into both Fallopian tubes.*

*16. The apparatus of claim 15 in which: the pump means comprises low pressure pump means for confining the forced material completely within the Fallopian tubes.*

*17. The apparatus of claim 14 in which: the second means includes further means operable to substantially divide dispensed material during the material moving process to provide sufficient material to each Fallopian tube.*

*18. The apparatus of claim 14 in which: the second means includes third means for selective expansion for substantially completely filling the uterine cavity.*

*19. The apparatus of claim 18 in which: the third means comprises means sufficiently flexible to generally conform to the shape of the uterine cavity when expanded to substantially completely fill the uterine cavity.*

*20. The apparatus of claim 18 including: control means connected to the first and third means for sequentially partially expanding the third means to displace the lower part of the uterine cavity, operating the first means to dispense material above the partially expanded third means, and fully expanding the third means to substantially completely fill the uterine cavity to force dispensed materials into both Fallopian tubes.*

*21. The apparatus of claim 20 in which: the control means includes low pressure means for expanding the third means to confine forced material within the Fallopian tubes.*

*22. The apparatus of claim 18 in which: the third means comprises balloon means.*

*23. The apparatus of claim 22 in which: the balloon means comprises a relaxed flexible substance having low surface tension and uniform expansion characteristics.*

*24. The apparatus of claim 23 in which: the balloon means substance comprises latex rubber.*

*25. Apparatus for dispensing material into the Fallopian tubes of a female body comprising: expandable sleeve means adapted to be positioned in the uterine cavity; first means for partially expanding the sleeve means to block the lower portion of the uterine cavity; second means for providing material into the uterine cavity between the partially expanded sleeve means and the fundus of the uterus; and the first means including further means for further expanding the sleeve means to substantially completely fill the uterine cavity to force material into both Fallopian tubes.*

*26. The apparatus of claim 25 including: means connected to the sleeve means for spacing the sleeve means a predetermined distance from the fundus of the uterus.*

*27. The apparatus of claim 25 in which: the sleeve means includes means operable on expansion for dividing the material into two portions before the sleeve means fills the uterine cavity.*

*28. The apparatus of claim 25 in which: the sleeve means comprises expandable tubular sheet material having low surface tension properties.*

*29. The apparatus of claim 25 in which: the further means includes means for expanding the sleeve means under low pressure to confine forced material within the Fallopian tubes.*

*30. Apparatus for dispensing materials into the Fallopian tubes of a female body comprising: catheter means having first and second isolated passages; pump means connected to the first passage; material dispensing means connected to the second passage for dispensing selected materials into a uterine cavity; and control means connected to the pump means and the dispensing means for automatically dispensing materials into the uterine cavity and forcing dispensed materials into both Fallopian tubes.*

*31. The apparatus of claim 30 in which: the pump means includes means for dividing dispensed materials into two portions prior to being forced into the Fallopian tubes.*

*32. The apparatus of claim 31 in which: the pump means is a low pressure pump means for inhibiting forcing materials completely through the Fallopian tubes.*

*33. The apparatus of claim 30 in which: the pump means comprises selectively expandable sleeve means.*

*34. The apparatus of claim 33 in which: the control means includes means for starting expansion of the sleeve means prior to the dispensing of materials into the uterine cavity, and for completing expansion of the sleeve means after the dispensing of materials.*

*35. The apparatus of claim 33 in which: the sleeve means comprises means sufficiently flexible to substantially completely fill the uterine cavity when expanded under generally low pressure.*

*36. The apparatus of claim 35 in which the sleeve means comprises a tubular sheet having low surface tension properties.*

*37. The apparatus of claim 33 in which: the control means includes means for providing fluid to the expandable sleeve means.*

*38. The apparatus of claim 30 in which: the control means extends out of the body when the pump means and the material dispensing means are in the uterine cavity.*

*39. The apparatus of claim 30 including: means connected to the control means for automatically sequentially dispensing materials and forcing the materials into the Fallopian tubes.*

*40. The apparatus of claim 33 including: means connected to the control means for automatically sequentially partially expanding the sleeve means, dispensing materials into the uterine cavity between the fundus and the partially expanded sleeve means and completing expansion of the sleeve means to force dispensed material into the Fallopian tubes.*

*41. Apparatus for non-surgically providing materials to both canals of the Fallopian tubes of a female comprising: means for containing material for movement into the canals of the Fallopian tubes; dispensing means having a first portion for moving the material from the means for containing material into the uterine cavity and a second portion for moving the material from the uterine cavity into the canals of the Fallopian tubes; and control means connected to the first and second portions for automatically operating the first portion to move material into the uterine cavity before operation of the second portion is completed.*

*42. Apparatus for non-surgically placing material in both canals of the Fallopian tubes of a female comprising: means for containing material for movement into the canals of the Fallopian tubes; dispensing means having expandable means positionable in the uterine cavity of the female and means for moving the material from the means for containing material into the uterine cavity; means for expanding the expandable means to substantially completely fill the uterine cavity for moving the materials from the uterine cavity into the canals of the Fallopian tubes; and control means connected to the means for moving the material and the means for expanding, for automatically moving the material into the uterine cavity before the expandable means substantially completely fills the uterine cavity.*

* * * * *

UNITED STATES PATENT AND TRADEMARK OFFICE

CERTIFICATE OF CORRECTION

PATENT NO. : RE 29,207

DATED : May 10, 1977

INVENTOR(S) : LEE R. BOLDUC and EUGENE A. DICKHUDT

It is certified that error appears in the above-identified patent and that said Letters Patent are hereby corrected as shown below:

Col. 1, Line 21, "canels" should be --canals--

Col. 5, Line 11, "cyanoacrylates, quinacrine" should read --cyanoacrylates. Quinacrine--.

Col. 9, Line 29, first line of Claim 32, "claim 31" should read --claim 30--.

Signed and Sealed this

*sixteenth* Day of *August 1977*

[SEAL]

*Attest:*

RUTH C. MASON
*Attesting Officer*

C. MARSHALL DANN
*Commissioner of Patents and Trademarks*